(12) United States Patent
Shen et al.

(10) Patent No.: US 11,684,463 B2
(45) Date of Patent: Jun. 27, 2023

(54) METHOD AND SYSTEM OF REPAIRING ORAL DEFECT MODEL

(71) Applicant: China Medical University, Taichung (TW)

(72) Inventors: Yen-Wen Shen, Taichung (TW); Lih-Jyh Fuh, Taichung (TW); Chi-Hsiung Yu, Toufen (TW)

(73) Assignee: China Medical University, Taichung (TW)

( * ) Notice: Subject to any disclaimer, the term of this patent is extended or adjusted under 35 U.S.C. 154(b) by 282 days.

(21) Appl. No.: 17/146,685

(22) Filed: Jan. 12, 2021

(65) Prior Publication Data

US 2021/0220094 A1 Jul. 22, 2021

(30) Foreign Application Priority Data

Jan. 16, 2020 (TW) ................................. 109101588

(51) Int. Cl.
*A61C 13/00* (2006.01)
*G06T 19/00* (2011.01)
*A61C 9/00* (2006.01)
*G16H 50/50* (2018.01)
(Continued)

(52) U.S. Cl.
CPC ........ *A61C 13/0004* (2013.01); *A61C 9/0046* (2013.01); *A61C 13/34* (2013.01); *G06T 19/00* (2013.01); *G16H 50/50* (2018.01); *A61C 5/77* (2017.02); *G06T 2210/41* (2013.01)

(58) Field of Classification Search
CPC ... A61C 13/0004; A61C 9/0046; A61C 13/34; A61C 5/77; G16H 50/50; G06T 19/00; G06T 2210/41
See application file for complete search history.

(56) References Cited

U.S. PATENT DOCUMENTS 6,227,850 B1 * 5/2001 Chishti .................... A61C 7/00
433/213
6,386,878 B1 * 5/2002 Pavlovskaia ......... A61C 9/0046
433/215

(Continued)

FOREIGN PATENT DOCUMENTS

| CN | 105761252 B | 3/2017 |
| CN | 105046750 B | 8/2017 |
| WO | 2011097947 A1 | 8/2011 |

*Primary Examiner* — Charles L Beard

(57) ABSTRACT

A method of repairing an oral defect model includes performing a three-dimensional oral defect model obtaining step, a defect cutting line detecting step, a defect point selecting step and a smoothing step. The three-dimensional oral defect model obtaining step is performed to scan an oral cavity to obtain a three-dimensional oral defect model message. The defect cutting line detecting step is performed to detect a defect cutting line of the three-dimension oral defect model message, and drive a displayer to display the defect cutting line. The defect point selecting step is performed to select at least one defect feature point of the defect cutting line via the displayer. The smoothing step is performed to perform a smoothing process at the at least one defect feature point, and convert the three-dimensional oral defect model message into a three-dimensional oral repaired model message to smooth the defect cutting line.

8 Claims, 11 Drawing Sheets

(51) Int. Cl.
*A61C 13/34* (2006.01)
*A61C 5/77* (2017.01)

(56) References Cited

U.S. PATENT DOCUMENTS

| | | | | |
|---|---|---|---|---|
| 6,463,344 | B1* | 10/2002 | Pavloskaia | G16H 50/50 |
| | | | | 700/118 |
| 10,631,956 | B1* | 4/2020 | Raslambekov | A61C 7/002 |
| 11,026,767 | B1* | 6/2021 | Raslambekov | G06T 7/12 |
| 11,191,618 | B1* | 12/2021 | Raslambekov | A61C 7/002 |
| 11,351,011 | B1* | 6/2022 | Raslambekov | G06T 19/20 |
| 11,478,336 | B1* | 10/2022 | Shao | G16H 30/20 |
| 11,553,969 | B1* | 1/2023 | Lang | G02B 27/0172 |
| 2002/0015934 | A1* | 2/2002 | Rubbert | A61C 7/146 |
| | | | | 433/29 |
| 2002/0055081 | A1* | 5/2002 | Hughes | A61C 7/00 |
| | | | | 433/213 |
| 2002/0055800 | A1* | 5/2002 | Nikolskiy | A61C 9/0046 |
| | | | | 700/98 |
| 2002/0177108 | A1* | 11/2002 | Pavlovskaia | A61C 5/77 |
| | | | | 433/213 |
| 2003/0139834 | A1* | 7/2003 | Nikolskiy | G06G 7/48 |
| | | | | 700/98 |
| 2003/0231805 | A1* | 12/2003 | Hultgren | G06T 19/00 |
| | | | | 382/128 |
| 2004/0023188 | A1* | 2/2004 | Pavlovskaia | A61C 9/00 |
| | | | | 433/213 |
| 2005/0043837 | A1* | 2/2005 | Rubbert | A61C 7/00 |
| | | | | 700/118 |
| 2006/0090361 | A1* | 5/2006 | Matsuda | G01B 11/24 |
| | | | | 33/514 |
| 2006/0263739 | A1* | 11/2006 | Sporbert | A61C 9/0053 |
| | | | | 433/213 |
| 2008/0154419 | A1* | 6/2008 | Cheng | G06T 19/00 |
| | | | | 700/118 |
| 2008/0261165 | A1* | 10/2008 | Steingart | B33Y 50/00 |
| | | | | 433/24 |
| 2009/0068617 | A1* | 3/2009 | Lauren | A61C 5/77 |
| | | | | 433/213 |
| 2009/0098502 | A1* | 4/2009 | Andreiko | A61C 7/002 |
| | | | | 433/24 |
| 2009/0148809 | A1* | 6/2009 | Kuo | G06F 30/00 |
| | | | | 433/68 |
| 2009/0162813 | A1* | 6/2009 | Glor | A61C 1/084 |
| | | | | 433/196 |
| 2009/0246726 | A1* | 10/2009 | Chelnokov | A61C 7/002 |
| | | | | 433/24 |
| 2010/0281370 | A1* | 11/2010 | Rohaly | G06T 15/205 |
| | | | | 715/810 |
| 2011/0196524 | A1* | 8/2011 | Giasson | B33Y 50/00 |
| | | | | 700/118 |
| 2011/0276159 | A1* | 11/2011 | Chun | A61C 13/0004 |
| | | | | 700/98 |
| 2013/0060532 | A1* | 3/2013 | Clausen | A61C 13/082 |
| | | | | 703/1 |
| 2013/0179126 | A1* | 7/2013 | Meier | G06F 30/00 |
| | | | | 703/1 |
| 2013/0209965 | A1* | 8/2013 | Fisker | A61C 19/04 |
| | | | | 433/220 |
| 2013/0218530 | A1* | 8/2013 | Deichmann | A61C 5/77 |
| | | | | 703/1 |
| 2014/0071126 | A1* | 3/2014 | Barneoud | G06T 17/00 |
| | | | | 345/420 |
| 2014/0142902 | A1* | 5/2014 | Chelnokov | A61C 7/002 |
| | | | | 703/1 |
| 2014/0278279 | A1* | 9/2014 | Azernikov | A61C 13/0003 |
| | | | | 703/1 |
| 2014/0316750 | A1* | 10/2014 | Jung | A61C 1/082 |
| | | | | 703/1 |
| 2015/0238289 | A1* | 8/2015 | Wouters | G05B 15/02 |
| | | | | 700/98 |
| 2015/0238290 | A1* | 8/2015 | Wouters | B29C 64/386 |
| | | | | 700/98 |
| 2015/0245890 | A1* | 9/2015 | Wouters | A61C 9/004 |
| | | | | 700/98 |
| 2016/0012182 | A1* | 1/2016 | Golay | G16H 40/20 |
| | | | | 705/3 |
| 2016/0224690 | A1* | 8/2016 | Lee | G16H 20/40 |
| 2016/0302896 | A1* | 10/2016 | Miller | A61C 13/083 |
| 2016/0374785 | A1* | 12/2016 | Fridzon | A61B 34/10 |
| | | | | 705/2 |
| 2017/0100214 | A1* | 4/2017 | Wen | G16H 30/20 |
| 2017/0273763 | A1* | 9/2017 | Fisker | A61C 9/0046 |
| 2017/0312058 | A1* | 11/2017 | Fisker | A61C 5/77 |
| 2018/0085203 | A1* | 3/2018 | Ramirez | A61C 5/77 |
| 2018/0116762 | A1* | 5/2018 | Kopelman | A61C 7/002 |
| 2018/0263726 | A1* | 9/2018 | Fares | A61C 5/20 |
| 2019/0043255 | A1* | 2/2019 | Somasundaram | G06T 17/20 |
| 2019/0066537 | A1* | 2/2019 | Van Den Braber | G06T 15/08 |
| 2019/0102880 | A1* | 4/2019 | Parpara | G06T 17/10 |
| 2019/0148005 | A1* | 5/2019 | Domracheva | G06T 19/20 |
| | | | | 345/424 |
| 2019/0164353 | A1* | 5/2019 | Yancey | A61C 9/004 |
| 2019/0197691 | A1* | 6/2019 | Chen | G06T 7/149 |
| 2019/0231492 | A1* | 8/2019 | Sabina | A61B 1/0646 |
| 2019/0337199 | A1* | 11/2019 | Jo | B29C 43/50 |
| 2019/0378344 | A1* | 12/2019 | Long | A61C 13/0004 |
| 2020/0005550 | A1* | 1/2020 | Schneider | A61C 13/34 |
| 2020/0008911 | A1* | 1/2020 | Savic | A61C 13/08 |
| 2020/0022790 | A1* | 1/2020 | Fisker | A61C 13/0024 |
| 2020/0125070 | A1* | 4/2020 | Krauser | A61C 13/0004 |
| 2020/0138551 | A1* | 5/2020 | Strong | A61C 13/34 |
| 2020/0197138 | A1* | 6/2020 | Parkar | A61C 13/087 |
| 2020/0281689 | A1* | 9/2020 | Yancey | A61B 5/0064 |
| 2020/0315744 | A1* | 10/2020 | Cramer | G16H 50/50 |
| 2020/0315754 | A1* | 10/2020 | Ciriello | A61B 90/14 |
| 2020/0320685 | A1* | 10/2020 | Anssari Moin | G06V 10/454 |
| 2020/0349698 | A1* | 11/2020 | Minchenkov | G06N 3/045 |
| 2020/0352678 | A1* | 11/2020 | Yuan | A61C 1/082 |
| 2021/0059796 | A1* | 3/2021 | Weiss | G06N 3/047 |
| 2021/0085238 | A1* | 3/2021 | Schnabel | A61B 5/4542 |
| 2021/0100642 | A1* | 4/2021 | Weiss | A61C 13/34 |
| 2021/0106403 | A1* | 4/2021 | Aptekarev | A61C 7/08 |
| 2021/0106410 | A1* | 4/2021 | Kim | A61C 13/0019 |
| 2021/0118132 | A1* | 4/2021 | Kearney | G06N 3/04 |
| 2021/0169318 | A1* | 6/2021 | Sorimoto | G06T 5/003 |
| 2021/0196430 | A1* | 7/2021 | Wilson | A61B 5/0088 |
| 2021/0200188 | A1* | 7/2021 | Shah | G06T 19/20 |
| 2021/0217233 | A1* | 7/2021 | Feng | G16H 50/50 |
| 2021/0244518 | A1* | 8/2021 | Ryu | G06T 19/20 |
| 2021/0272377 | A1* | 9/2021 | Nikolskiy | A61C 5/77 |
| 2021/0304874 | A1* | 9/2021 | Nikolskiy | A61C 5/77 |
| 2021/0353386 | A1* | 11/2021 | Raby | A61C 7/10 |
| 2021/0353394 | A1* | 11/2021 | Lee | A61C 13/34 |
| 2021/0357688 | A1* | 11/2021 | Kearney | G16H 50/70 |
| 2021/0365736 | A1* | 11/2021 | Kearney | A61B 1/000096 |
| 2022/0000592 | A1* | 1/2022 | Ramirez | G06F 30/00 |
| 2022/0008175 | A1* | 1/2022 | Öjelund | G06N 20/20 |
| 2022/0031433 | A1* | 2/2022 | Diez | A61C 13/0004 |
| 2022/0036653 | A1* | 2/2022 | De Somere | G06T 19/20 |
| 2022/0047358 | A1* | 2/2022 | Domroese | A61C 7/08 |
| 2022/0079714 | A1* | 3/2022 | Paraketsov | G06T 17/20 |
| 2022/0087791 | A1* | 3/2022 | Choi | A61B 90/39 |
| 2022/0117480 | A1* | 4/2022 | Kaji | A61B 1/24 |
| 2022/0139044 | A1* | 5/2022 | Koza | G06T 19/006 |
| | | | | 345/419 |
| 2022/0160476 | A1* | 5/2022 | Kim | A61B 5/743 |
| 2022/0166955 | A1* | 5/2022 | Gronau | G06T 19/20 |
| 2022/0172430 | A1* | 6/2022 | Träff | G06V 10/7747 |
| 2022/0180012 | A1* | 6/2022 | Chiosa | G06T 17/20 |
| 2022/0183771 | A1* | 6/2022 | Cho | G16H 50/50 |
| 2022/0183789 | A1* | 6/2022 | Ciriello | G16H 30/40 |
| 2022/0192786 | A1* | 6/2022 | Chelnokov | A61C 7/002 |
| 2022/0207737 | A1* | 6/2022 | Parpara | G06T 7/0014 |
| 2022/0222910 | A1* | 7/2022 | Salah | G06F 18/2413 |
| 2022/0246270 | A1* | 8/2022 | Alvarez | G16H 20/40 |
| 2022/0262007 | A1* | 8/2022 | Cramer | G06V 10/774 |
| 2022/0304782 | A1* | 9/2022 | Derzapf | G16H 40/67 |
| 2022/0313402 | A1* | 10/2022 | Katzman | A61C 7/002 |

(56) References Cited

U.S. PATENT DOCUMENTS

2022/0331072 A1* 10/2022 Song ................. A61C 9/006
2022/0338966 A1* 10/2022 Lancelle ............ A61B 5/4547

* cited by examiner

METHOD AND SYSTEM OF REPAIRING ORAL DEFECT MODEL

RELATED APPLICATIONS

This application claims priority to Taiwan Application Serial Number 109101588, filed Jan. 16, 2020, which is herein incorporated by reference.

BACKGROUND

Technical Field

The present disclosure relates to a repairing method and a repairing system. More particularly, the present disclosure relates to a method of repairing an oral defect model and a system of repairing the oral defect model.

Description of Related Art

Teeth of the oral often cause to conditions of dentine abrasivity or missing tooth by serious cavities, injury, periodontal diseases or congenital missing tooth. Generally, dentists make the fixed dental crown, dental bridge or removable artificial teeth according to the condition of the missing tooth of the patient to recovery the demand of the chewing, pronunciation and appearance. If the abutment teeth of the patient can meet the requirement, the fixed artificial crown may be first priority.

The conventional techniques can obtain a model of artificial abutment teeth by a conventional impression or a digital intraoral scanner. The model is poured after conventional impression, followed by a step of ditching is performed to complete a die. There might be defects in both conventional and digital impression method caused by saliva, blood, air bubbles, etc. causing incontinuous finish line or prepared abutment surfaces. The technicians modified the model by their self-experience with a magnifier.

Thus, a method and a system of repairing the oral defect model utilize the automation and artificial intelligence algorithm instead of conventional human experience to reduce the deviation caused by human are commercially desirable.

SUMMARY

According to one aspect of the present disclosure, a method of repairing an oral defect model is performed. The method of repairing the oral defect model includes performing a three-dimensional oral defect model obtaining step, a defect cutting line detecting step, a defect point selecting step and a smoothing step. The three-dimensional oral defect model obtaining step is performed to drive a scanner to scan an oral cavity to obtain a three-dimensional oral defect model message. The defect cutting line detecting step is performed to drive a processor to detect a defect cutting line of the three-dimension oral defect model message, and drive a displayer to display the defect cutting line. The defect cutting line includes at least one defect feature point. The defect point selecting step is performed to select the at least one defect feature point of the defect cutting line via the displayer. The smoothing step is performed to drive the processor to perform a smoothing process at the at least one defect feature point, and convert the three-dimensional oral defect model message into a three-dimensional oral repaired model message to smooth the defect cutting line.

According to another aspect of the present disclosure, a method of repairing an oral defect model is performed. The method of repairing the oral defect model includes performing a three-dimensional oral defect model obtaining step, a defect cutting line detecting step, a defect point selecting step and a smoothing step. The three-dimensional oral defect model obtaining step is performed to drive a scanner to scan an oral cavity model to obtain a three-dimensional oral defect model message. The defect cutting line detecting step is performed to drive a processor to detect a defect cutting line of the three-dimension oral defect model message, and drive a displayer to display the defect cutting line. The defect cutting line includes at least one defect feature point. The defect point selecting step is performed to select the at least one defect feature point of the defect cutting line via the displayer. The smoothing step is performed to drive the processor to perform a smoothing process at the at least one defect feature point, and convert the three-dimensional oral defect model message into a three-dimensional oral repaired model message to smooth the defect cutting line.

According to further another aspect of the present disclosure, a system of repairing an oral defect model includes a scanner, a processor and a displayer. The scanner is configured to scan one of an oral cavity and an oral cavity model to obtain a three-dimensional oral defect model message. The processor is signally connected to the scanner, the processor receives the three-dimensional oral defect model message and includes a defect cutting line detecting module, a defect point selecting module and a smoothing module. The defect cutting line detecting module detects a defect cutting line of the three-dimensional oral defect model message, and the defect cutting line includes at least one defect feature point. The defect point selecting module is signally connected to the defect cutting line detecting module. The defect point selecting module selects the at least one defect feature point of the defect cutting line. The smoothing module is signally connected to the defect point selecting module. The smoothing module performs a smoothing process at the at least one defect feature point, and converts the three-dimensional oral defect model message into a three-dimensional oral repaired model message to smooth the defect cutting line. The displayer is signally connected to the processor, and the displayer displays the three-dimensional oral defect model message, the defect cutting line and the three-dimensional oral repaired model message.

BRIEF DESCRIPTION OF THE DRAWINGS

The present disclosure can be more fully understood by reading the following detailed description of the embodiment, with reference made to the accompanying drawings as follows.

DETAILED DESCRIPTION

The embodiment will be described with the drawings. For clarity, some practical details will be described below. However, it should be noted that the present disclosure should not be limited by the practical details, that is, in some embodiment, the practical details is unnecessary. In addition, for simplifying the drawings, some conventional structures and elements will be simply illustrated, and repeated elements may be represented by the same labels.

It will be understood that when an element (or device) is referred to as be "connected to" another element, it can be directly connected to the other element, or it can be indirectly connected to the other element, that is, intervening elements may be present. In contrast, when an element is referred to as be "directly connected to" another element, there are no intervening elements present. In addition, the terms first, second, third, etc. are used herein to describe various elements or components, these elements or components should not be limited by these terms. Consequently, a first element or component discussed below could be termed a second element or component.

Figure 1:
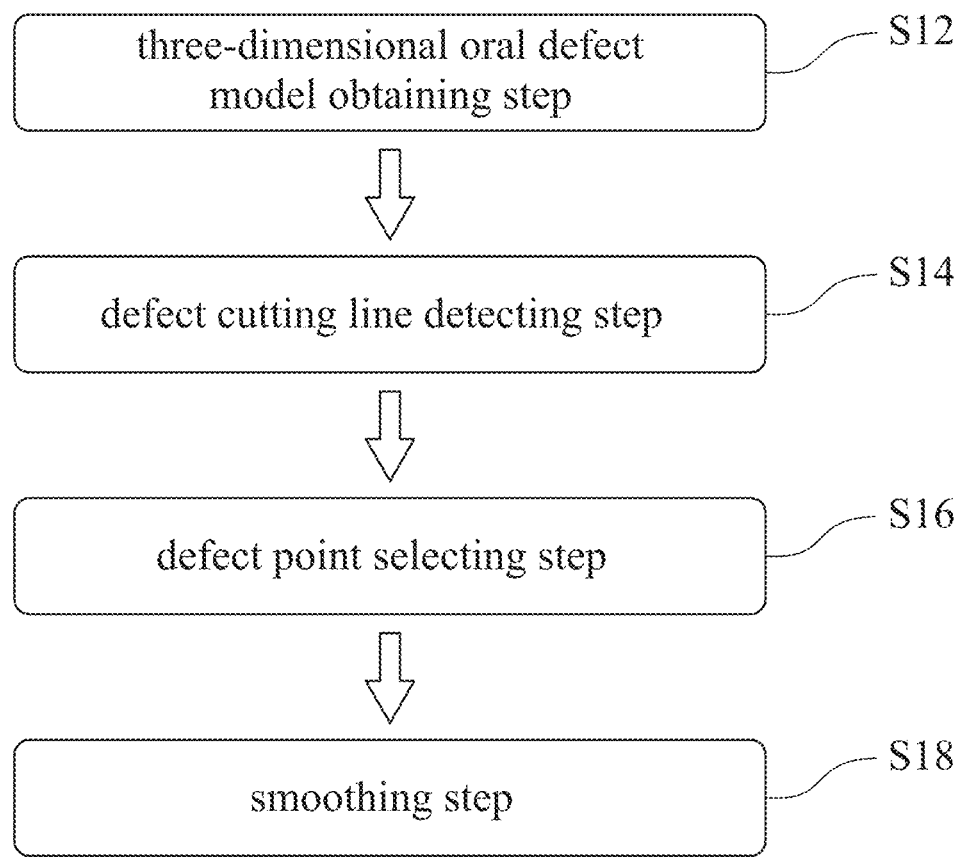
FIG. 1 shows a flow chart of a method of repairing an oral defect model according to an embodiment of the present disclosure.
Figure 2:
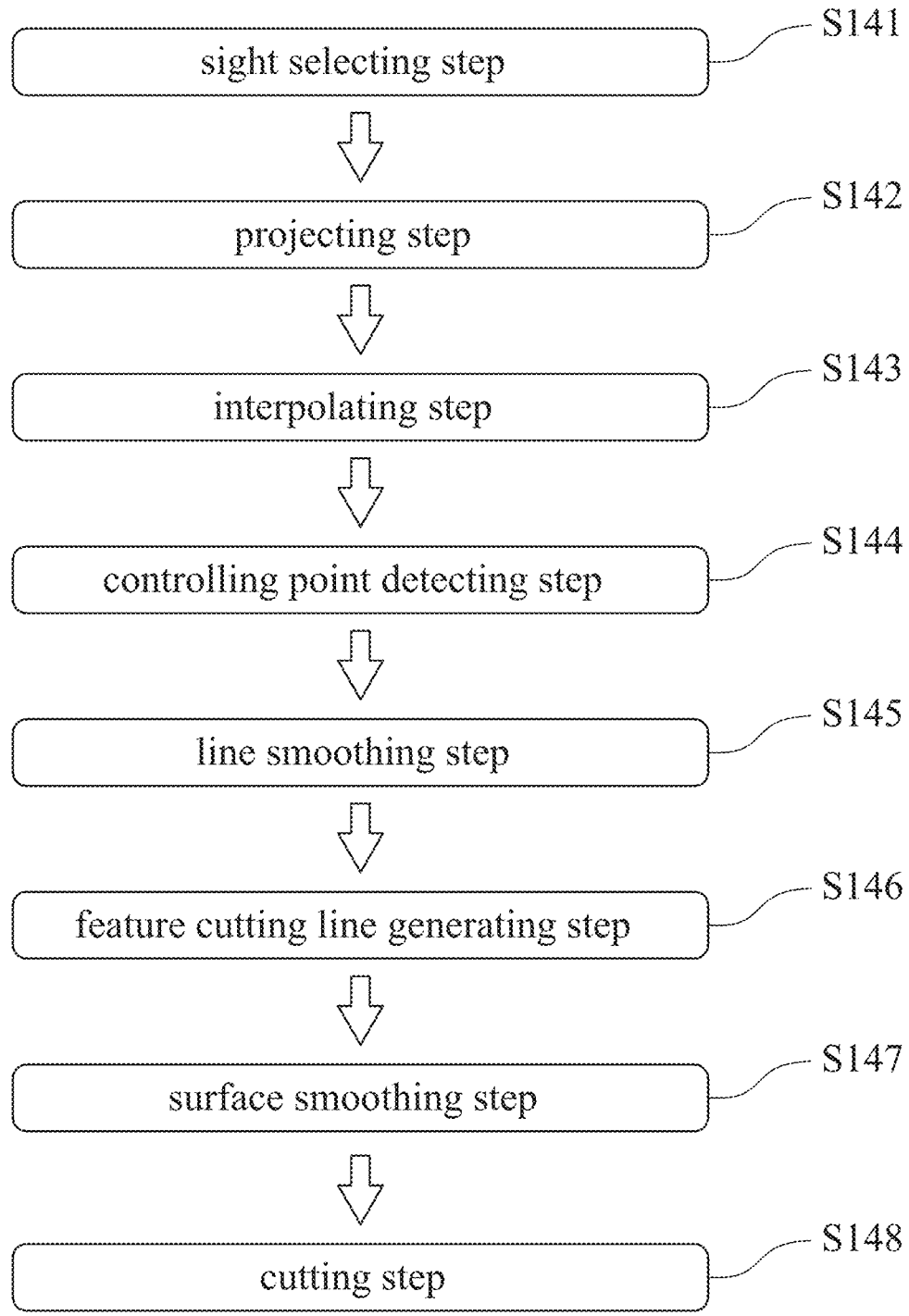
FIG. 2 shows a flow chart of a defect cutting line detecting step of FIG. 1.
Figure 3:
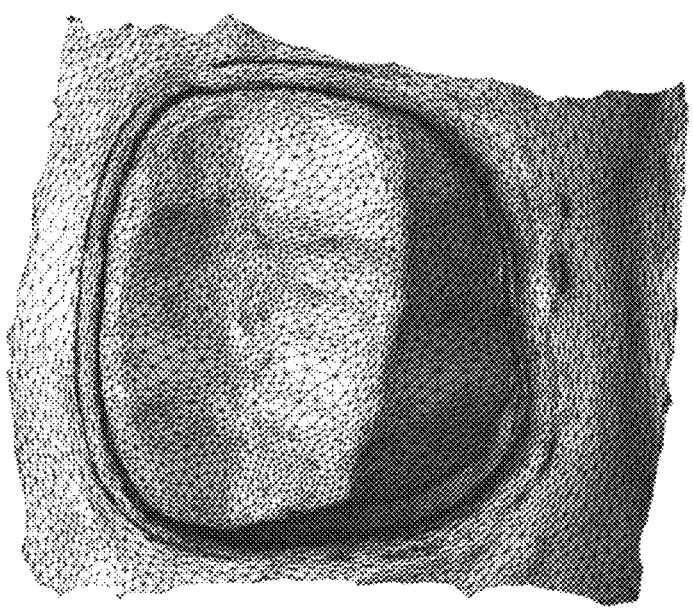
FIG. 3 shows a schematic view of a sight selecting step of FIG. 2.
Figure 3:
Figure 3:
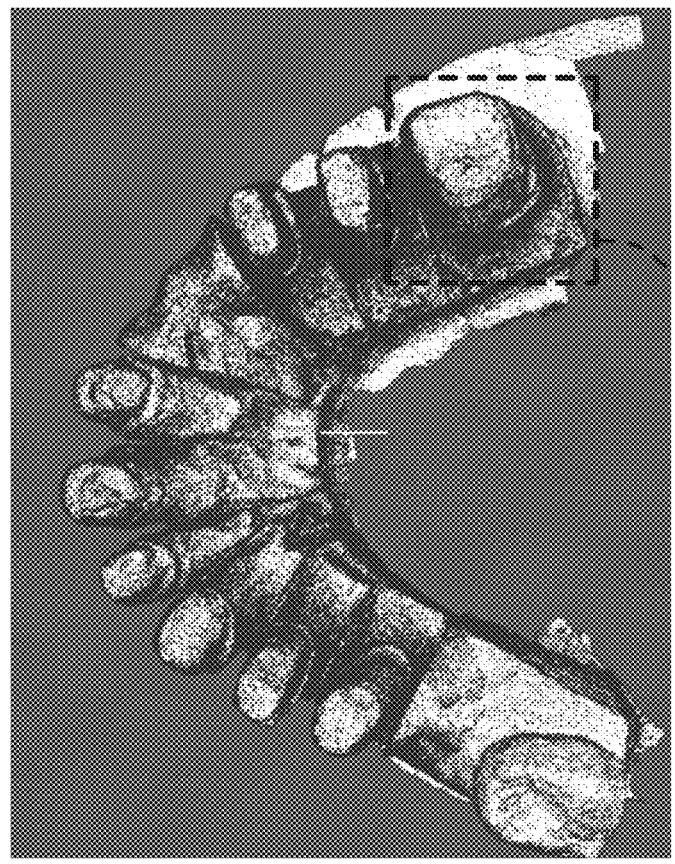
Figure 4:
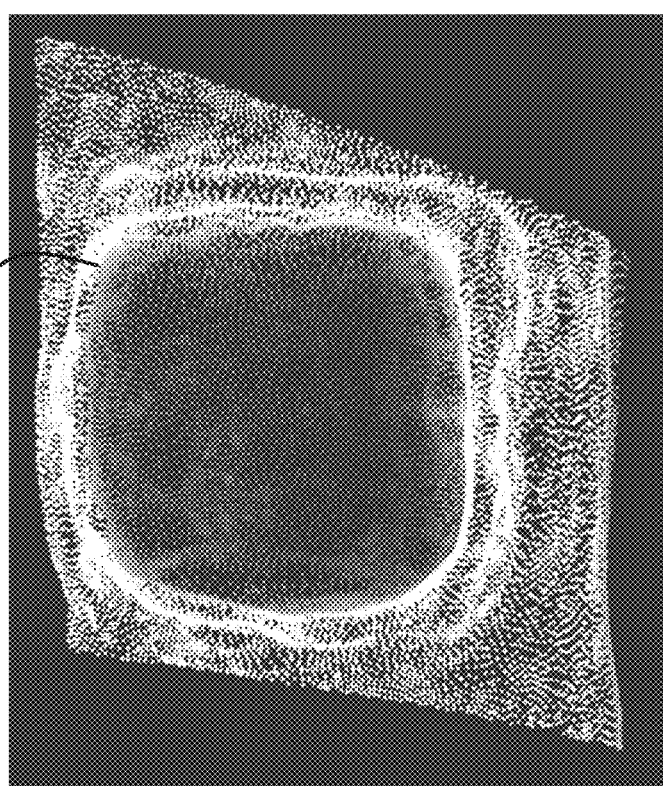
FIG. 4 shows a schematic view of a projecting step of FIG. 2.
Figure 4:
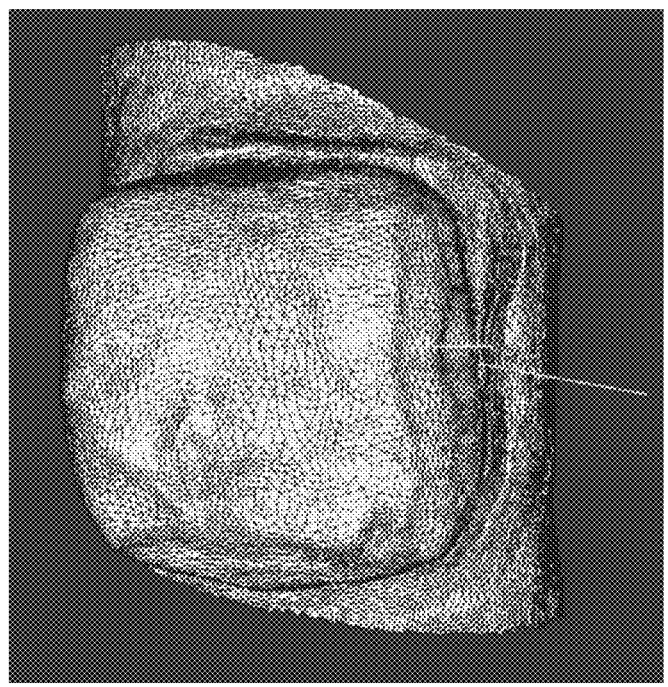
Figure 5:
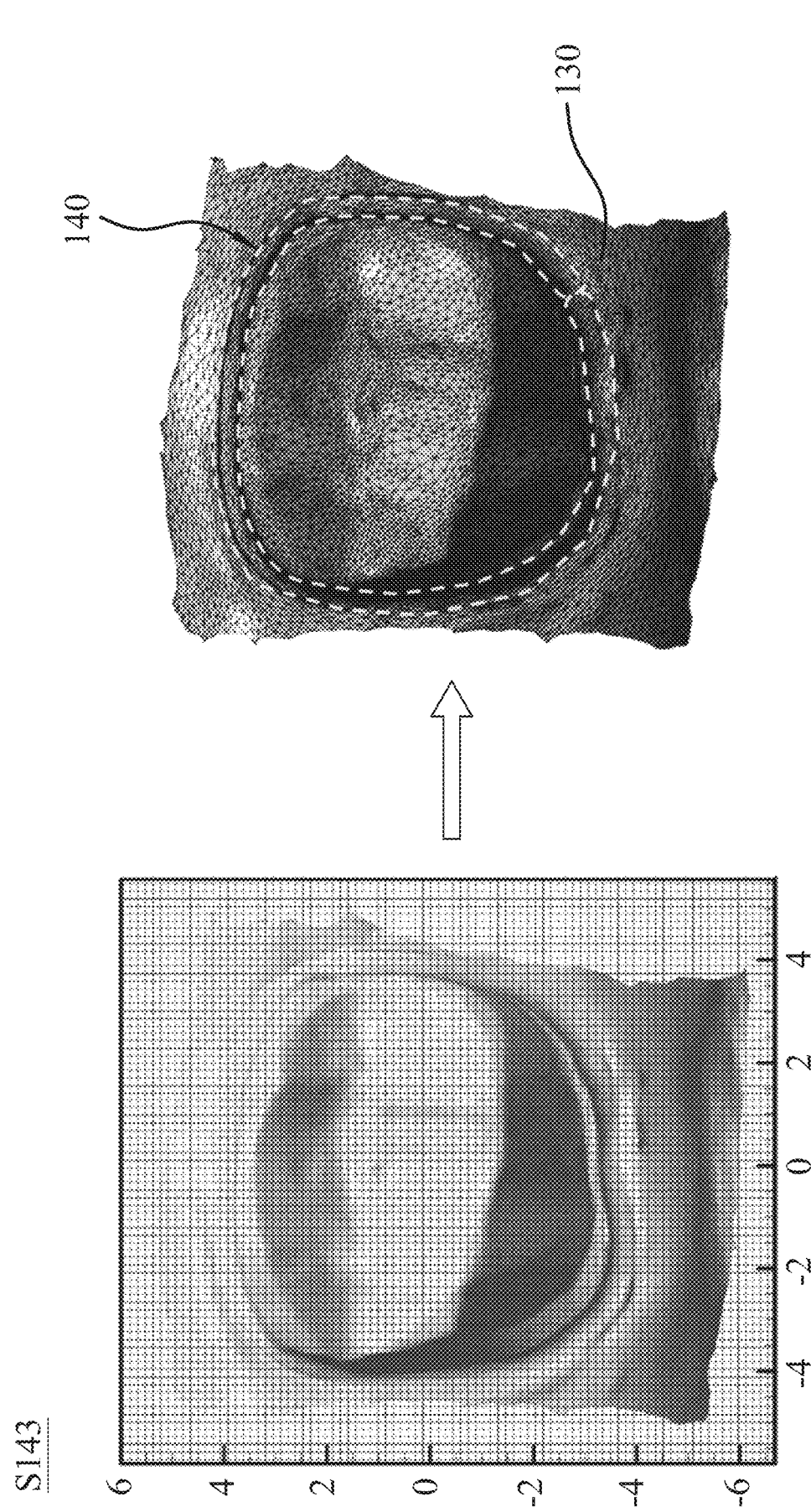
FIG. 5 shows a schematic view of an interpolating step of FIG. 2.
Figure 6:
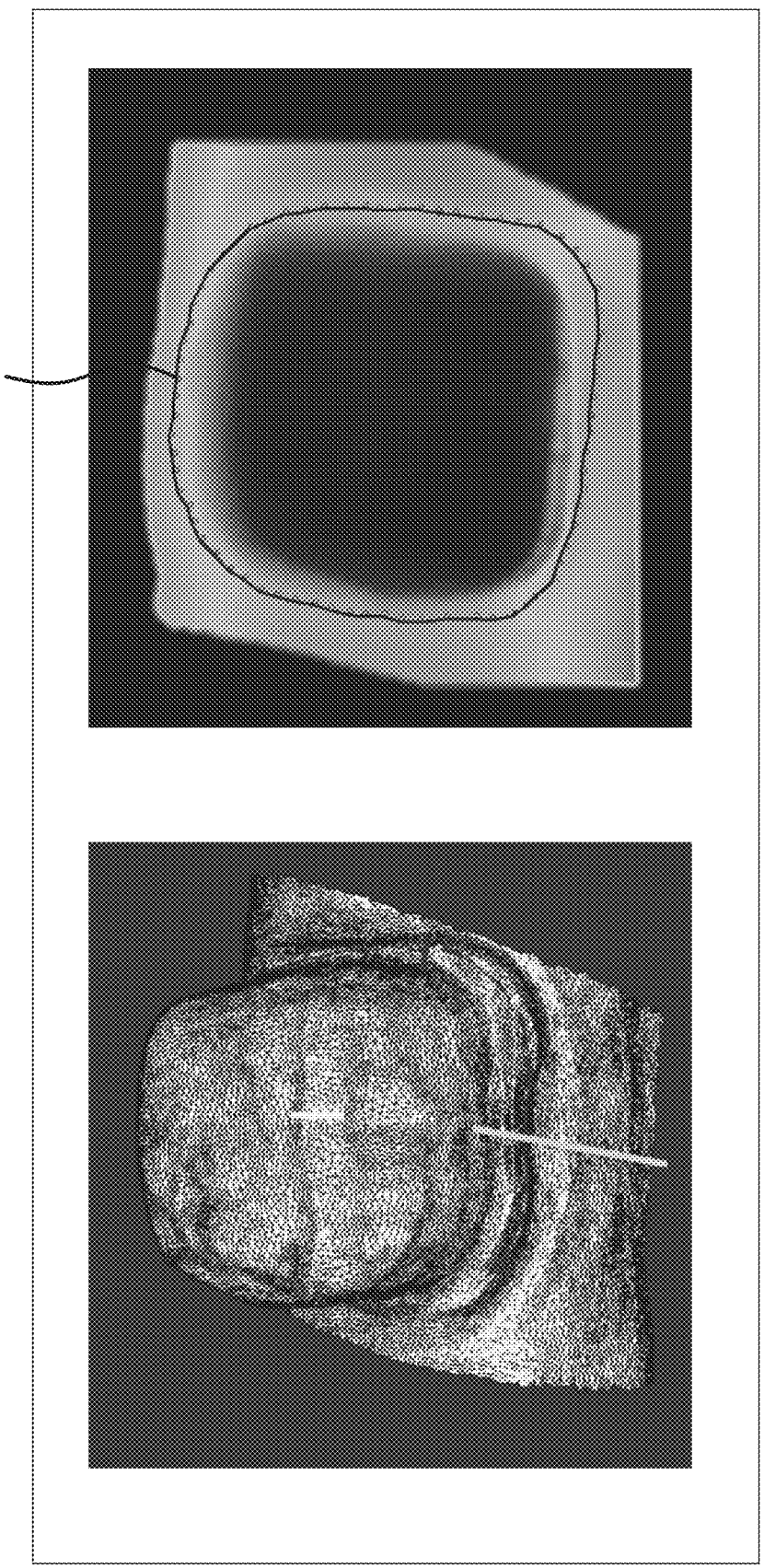
FIG. 6 shows a schematic view of a controlling point detecting step of FIG. 2.
Figure 7:
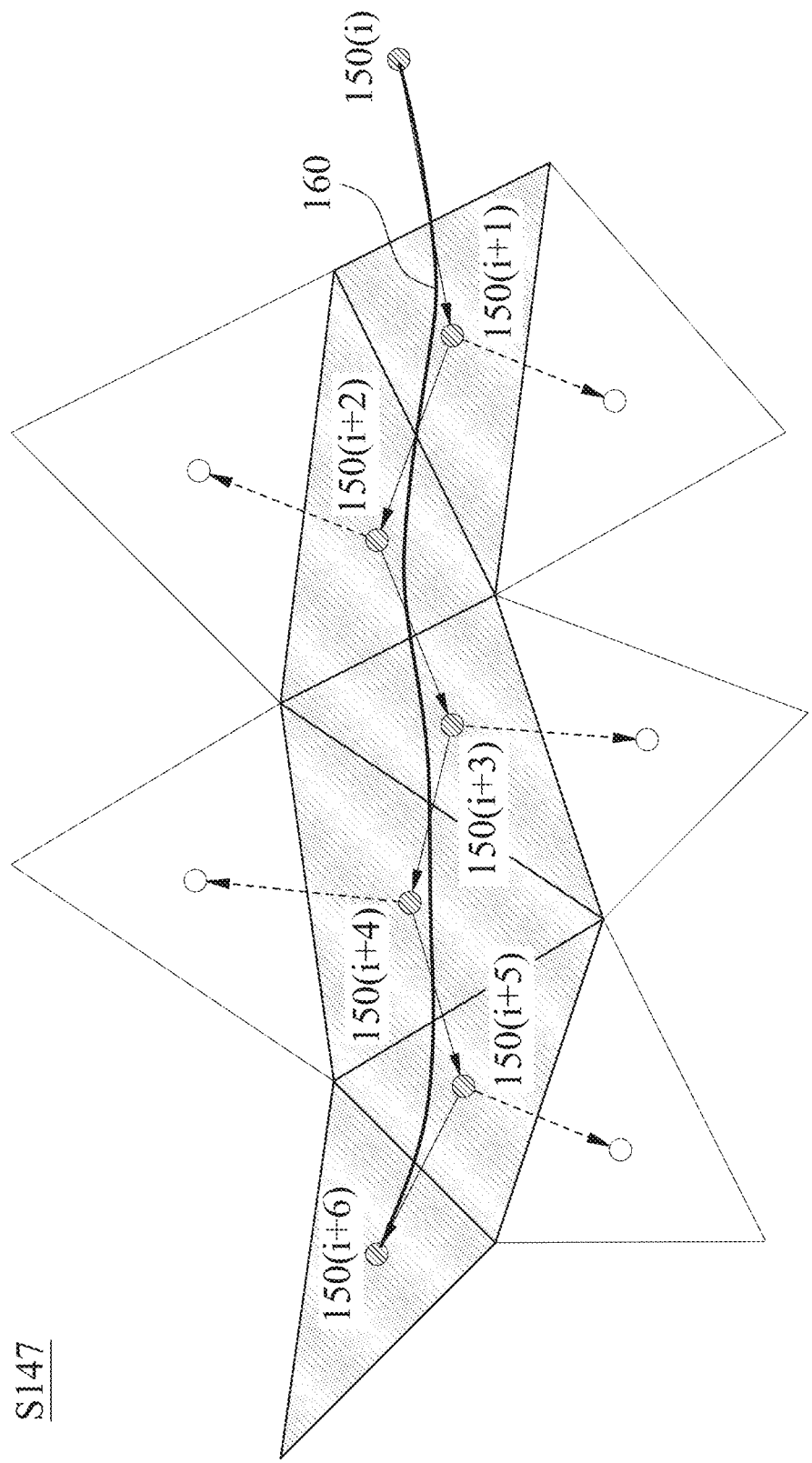
FIG. 7 shows a schematic view of a surface smoothing step of FIG. 2.
Figure 8:
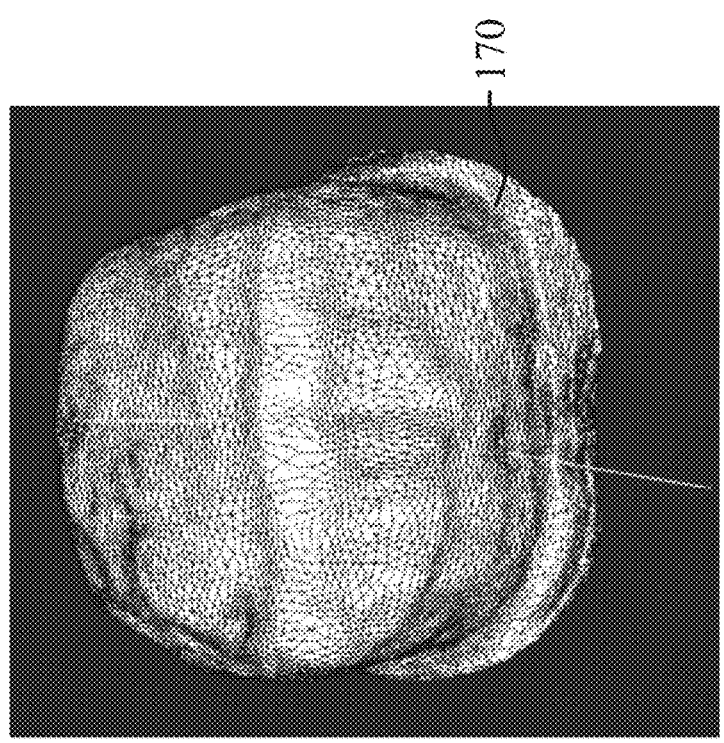
FIG. 8 shows a schematic view of a cutting step of FIG. 2.
Figure 8:
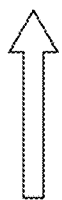
Figure 8:
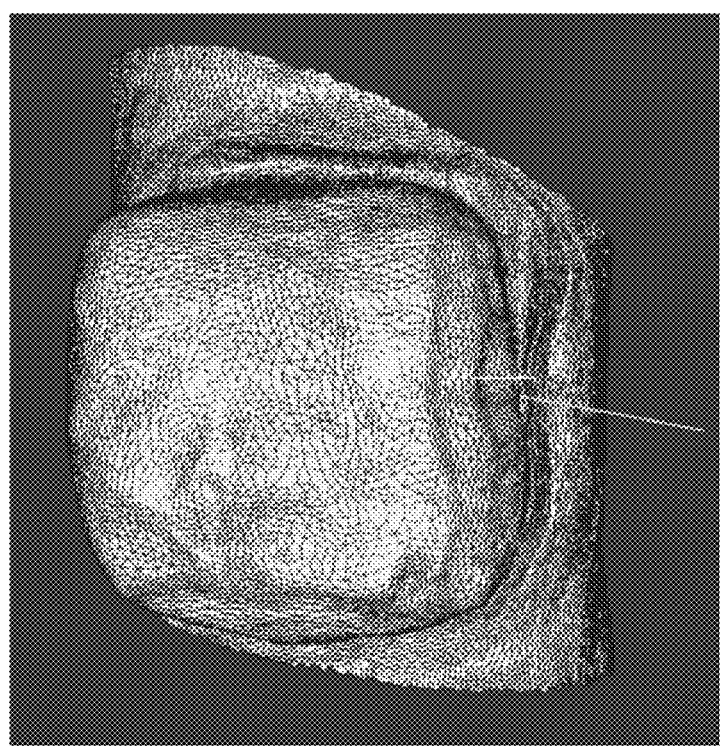
Figure 9:
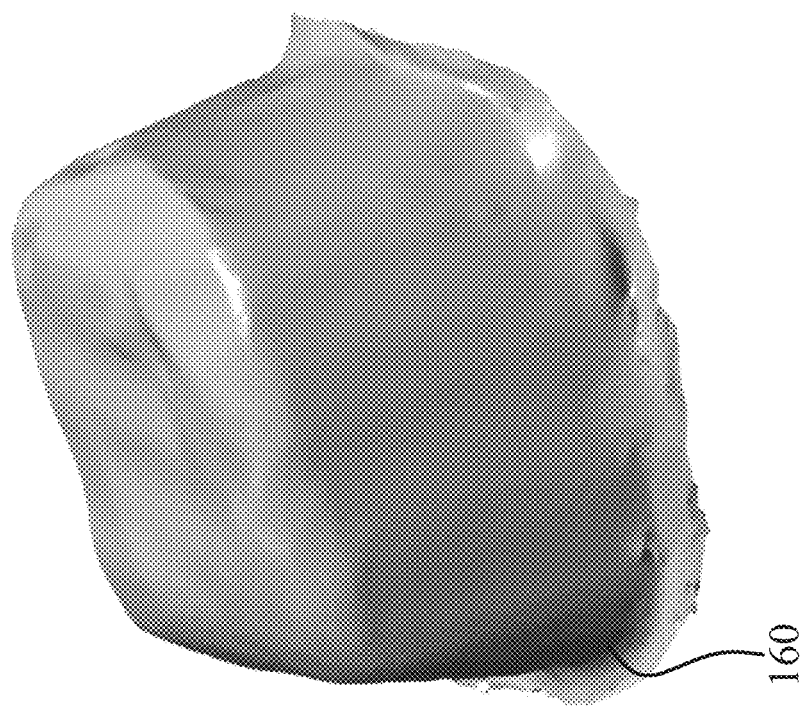
FIG. 9 shows a schematic view of a defect point selecting step and a smoothing step of FIG. 1.
Figure 9:
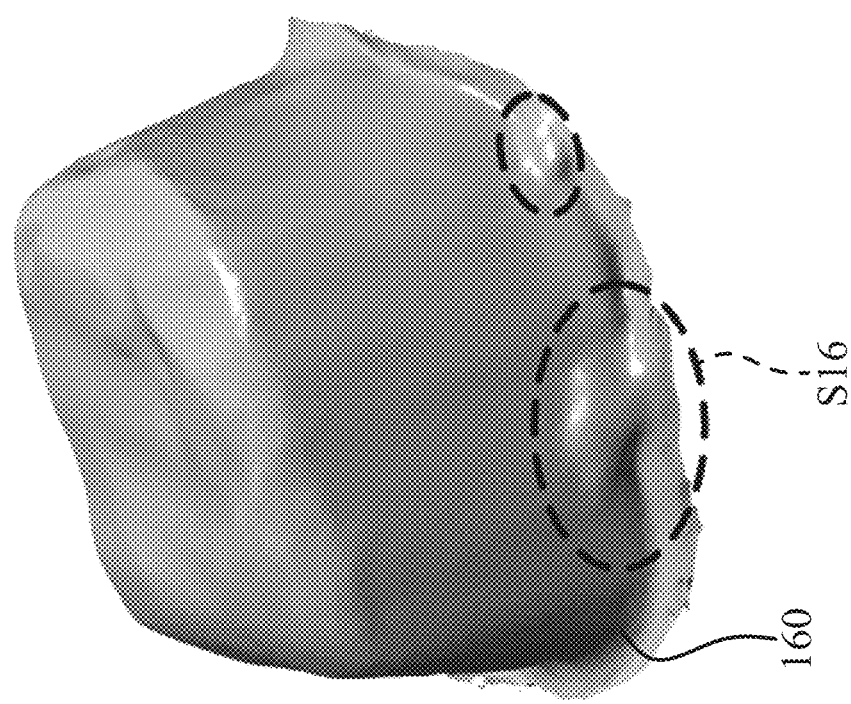

Please refer to FIG. 1 to FIG. 9. FIG. 1 shows a flow chart of a method 100 of repairing an oral defect model according to an embodiment of the present disclosure. FIG. 2 shows a flow chart of a defect cutting line detecting step S14 of FIG. 1. FIG. 3 shows a schematic view of a sight selecting step S141 of FIG. 2. FIG. 4 shows a schematic view of a projecting step S142 of FIG. 2. FIG. 5 shows a schematic view of an interpolating step S143 of FIG. 2. FIG. 6 shows a schematic view of a controlling point detecting step S144 of FIG. 2. FIG. 7 shows a schematic view of a surface smoothing step S147 of FIG. 2. FIG. 8 shows a schematic view of a cutting step S148 of FIG. 2. FIG. 9 shows a schematic view of a defect point selecting step S16 and a smoothing step S18 of FIG. 1. The method 100 of repairing the oral defect model includes performing a three-dimensional oral defect model obtaining step S12, the defect cutting line detecting step S14, the defect point selecting step S16 and the smoothing step S18.

The three-dimensional oral defect model obtaining step S12 is performed to drive a scanner to scan an oral cavity to obtain a three-dimensional oral defect model message.

The defect cutting line detecting step S14 is performed to drive a processor to detect a defect cutting line 160 of the three-dimension oral defect model message, and drive a displayer to display the defect cutting line 160. The defect cutting line 160 includes at least one defect feature point. In detail, the defect cutting line detecting step S14 includes the sight selecting step S141, the projecting step S142, the interpolating step S143, the controlling point detecting step S144, a line smoothing step S145, a feature cutting line generating step S146, the surface smoothing step S147 and the cutting step S148.

The sight selecting step S141 is performed to select an abutment region 110 of the three-dimensional oral defect model message, and observe the abutment region 110 from a top view of the abutment region 110, as shown in FIG. 3.

In other words, the sight selecting step S141 only analyzes single abutment impression, because the three-dimensional model message which includes upper teeth and lower teeth may be big enough to cause problems of a serious delay and the long calculating and analyzing time. To avoid the aforementioned problems, the sight selecting step S141 only analyzes the single abutment region 110.

The projecting step S142 is performed to project the three-dimensional oral defect model message in the abutment region 110 to a two-dimensional plane according to the top view of the abutment region 110 so as to form a two-dimensional projecting point set 120, as shown in FIG. 4. Moreover, the projecting step S142 records elevation values of each point of the two-dimensional projecting point set 120, and the elevation values of each point of the two-dimensional projecting point set 120 will be used in the following steps. In FIG. 4, the left diagram is a three-dimensional diagram; the right diagram is a two-dimensional diagram.

The interpolating step S143 is performed to perform an orthogonal grid interpolation method at the two-dimensional projecting point set 120 to obtain a two-dimensional concentrated projecting point set 130 as shown in FIG. 5. The orthogonal grid interpolation method of the present disclosure is an inverse distance weighted (IDW) method, but the present disclosure is not limited thereto. The IDW method utilizes the weighted value of the adjacent known point to estimate a variable of the present position. The weighted way is inversely proportional to the degree of the distance, that is, the greater of the distance the smaller of the weighted number, otherwise, the smaller of the distance, the greater of the weighted number. In the interpolating step S143, a dot density of the two-dimensional concentrated projecting point set 130 is greater than a dot density of the two-dimensional projecting point set 120.

The controlling point detecting step S144 is performed to search a feature region 140 with an annular shape in an equal angle (for example, in 5 degrees) and a radially way out from a departure point, and then search a plurality of triangular grids of the feature region 140. The triangular grids are viewed as a plurality of controlling points 150, as shown in FIG. 5 and FIG. 6. The departure point is determined as a model center of the two-dimensional concentrated projecting point set 130. In FIG. 6, the left diagram is a three-dimensional diagram; the right diagram is a two-dimensional diagram.

The line smoothing step S145 is performed to perform a weighted moving average method at the controlling points 150 to smooth the feature region 140. The feature region 140 and the controlling points 150 are positioned on the two-dimensional plane, and the weighted moving average method is the prior art and will not be described herein again.

The feature cutting line generating step S146 is performed to generate a feature cutting lie from the controlling points 150 smoothed by the line smoothing step S145. FIG. 7 shows seven controlling points 150(i), 150(i+1), 150(i+2), 150(i+3), 150(i+4), 150(i+5) and 150(i+6). The solid arrow in FIG. 7 represents a correct searching direction of the next controlling point, and the dashed arrow in FIG. 7 represents an incorrect searching direction of the next controlling point.

The surface smoothing step S147 is performed to perform the weighted moving average method at the feature cutting line to generate the defect cutting line 160, and the defect cutting line 160 is in a closed loop shape, as shown in FIG. 7.

The cutting step S148 is performed to cut the defect cutting line 160 to obtain a three-dimensional abutment model 170, as shown in FIG. 8. The three-dimensional abutment model 170 can be saved as a format of stereo lithography file (STL File).

The defect point selecting step S16 is performed to select the at least one defect feature point of the defect cutting line 160 via the displayer, as shown in FIG. 9.

The smoothing step S18 is performed to drive the processor to perform a smoothing process at the at least one defect feature point, and convert the three-dimensional oral defect model message into a three-dimensional oral repaired model message to smooth the defect cutting line 160 in FIG. 9. Thus, the method 100 of repairing the oral defect model of the present disclosure utilizes the smoothing process to repair the defect cutting line 160 of the defective region into a smooth edge line, so that the uncomfortable feeling and pressure formed by a dentist obtaining an ideal model can be reduced, and deviation caused by human can also be reduced, thereby manufacturing tight artificial teeth and increase the medical quality.

Figure 10:
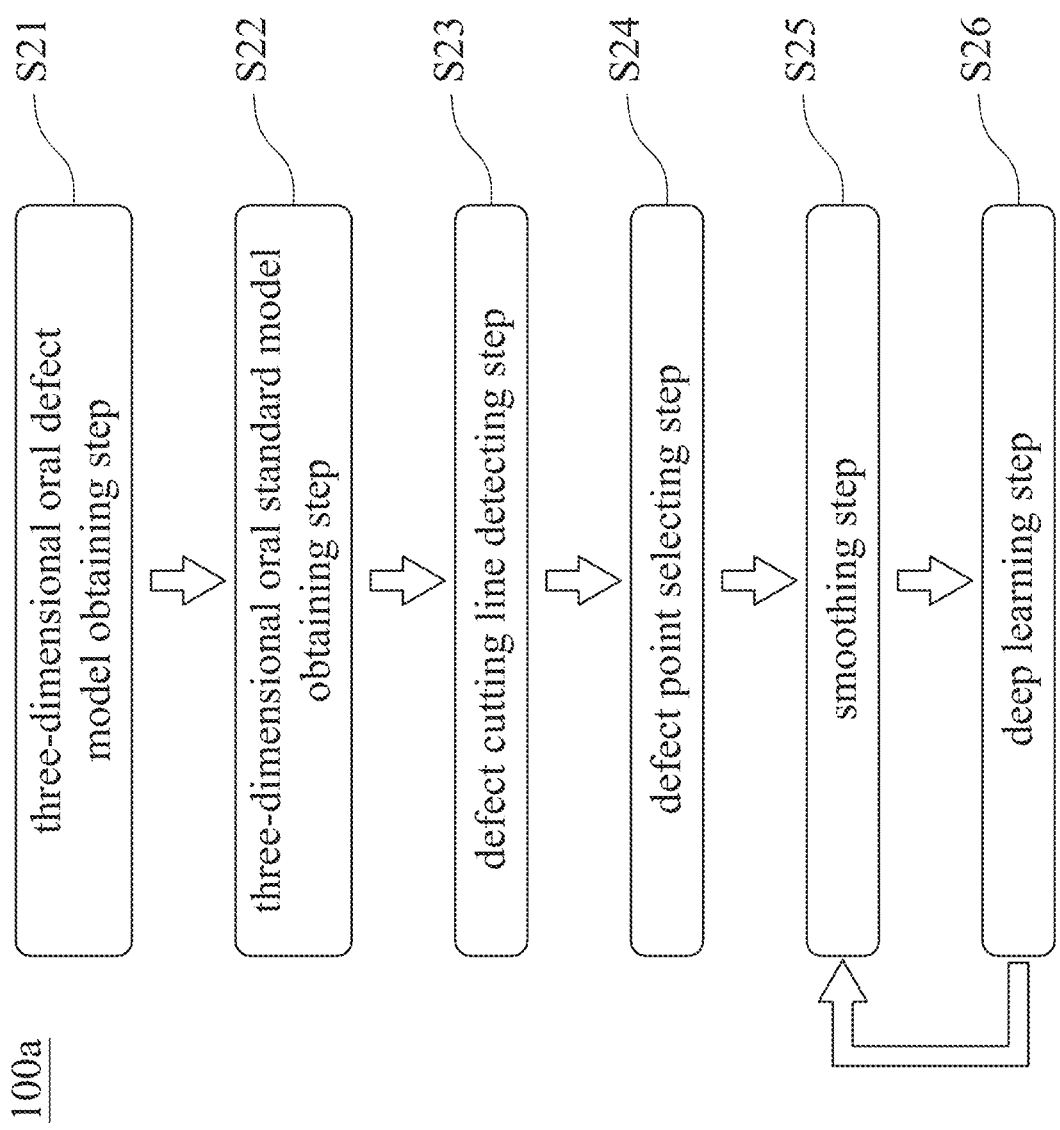
FIG. 10 shows a flow chart of a method of repairing an oral defect model according to another embodiment of the present disclosure.

Please refer to FIG. 1, FIG. 2 and FIG. 10. FIG. 10 shows a flow chart of a method 100a of repairing an oral defect model according to another embodiment of the present disclosure. The method 100a of repairing the oral defect model includes a three-dimensional oral defect model obtaining step S21, a three-dimensional oral standard model obtaining step S22, a defect cutting line detecting step S23, a defect point selecting step S24, a smoothing step S25 and a deep learning step S26.

The three-dimensional oral defect model obtaining step S21 is performed to drive a scanner to scan an oral cavity model to obtain a three-dimensional oral defect model message. The oral cavity model can be a plaster tooth model after an impression, or a model or a scanning generated by artificial intelligence. The three-dimensional oral standard model obtaining step S22 is performed to obtain a three-dimensional oral standard model message from a database, and the three-dimensional oral standard model message is corresponding to the oral cavity. A defect difference exists between the three-dimensional oral defect model message and the three-dimensional oral standard model message. The three-dimensional oral standard model message can be a plaster tooth model ditched by a technician with full experience.

The defect cutting line detecting step S23, the defect point selecting step S24 and the smoothing step S25 are the same as the defect cutting line detecting step S14, the defect point selecting step S16 and the smoothing step S18 in FIG. 1, respectively. A smoothing difference exists between the three-dimensional oral repaired model message generated from the smoothing step S25 and the three-dimensional oral standard model message. In one embodiment of the present disclosure, the three-dimensional oral defect model message, the three-dimensional oral repaired model message and the three-dimensional oral standard model message are all in the format of STL File.

The deep learning step S26 is performed to drive the processor to perform a deep learning algorithm at the three-dimensional oral repaired model message and the three-dimensional oral standard model message to train the smoothing process and reduce the smoothing difference. The deep learning algorithm is the prior art, and will not be described again. Thus, the method 100a of repairing the oral defect model of the present disclosure can let the defect difference greater than the smoothing difference, in other words, the three-dimensional oral repaired model message generated by the present disclosure can approach the three-dimensional oral standard model message. The method 100a utilizes the automation and artificial intelligence algorithm instead of conventional human experience to reduce the uncomfortable feeling and pressure formed by a dentist obtaining an ideal model, and reduce the deviation caused by human so as to manufacture tight artificial teeth and increase the medical quality.

Figure 11:
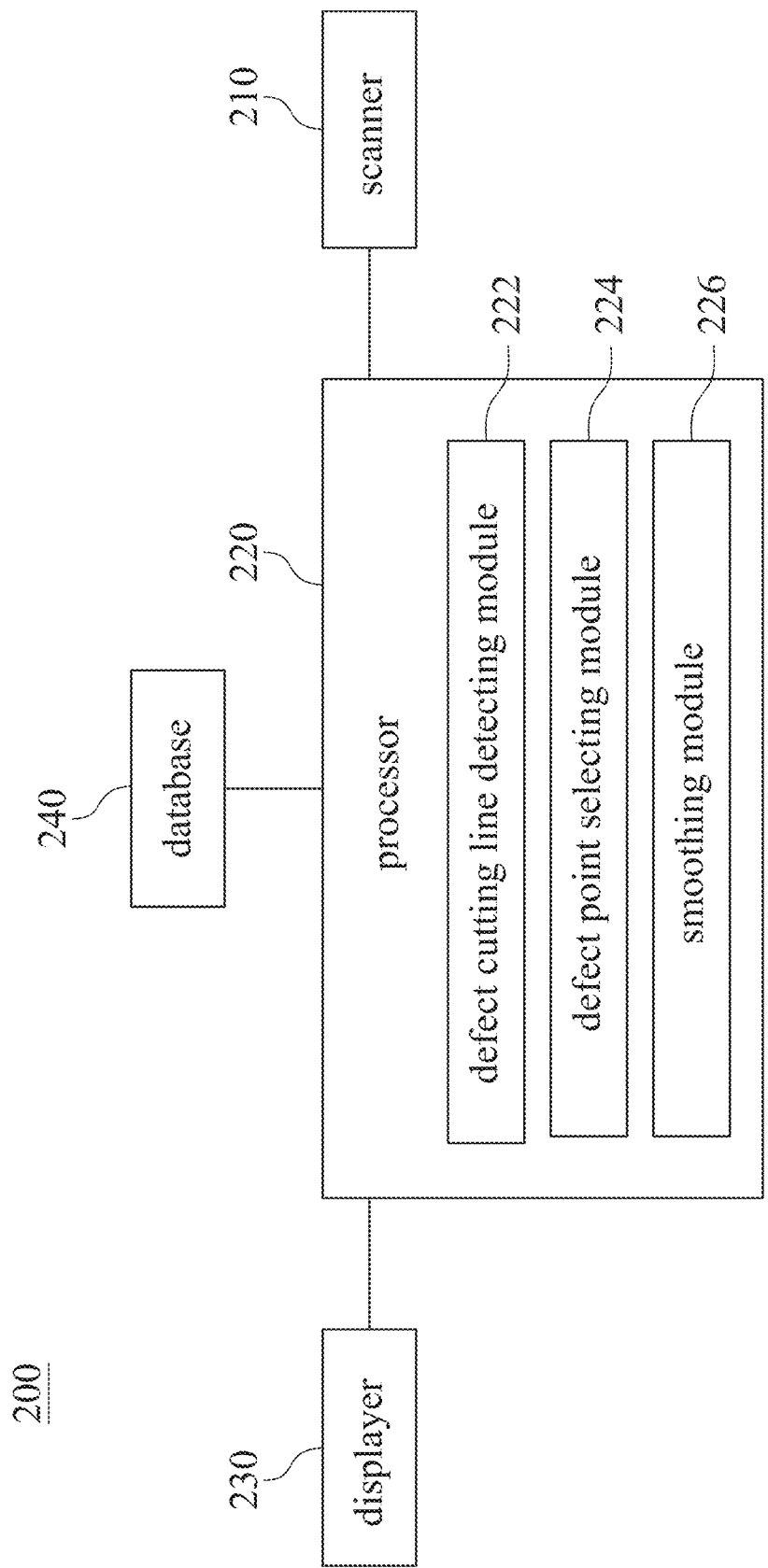
FIG. 11 shows a schematic view of a system of repairing an oral defect model according to further another embodiment of the present disclosure.

Please refer to FIG. 11. FIG. 11 shows a schematic view of a system 200 of repairing an oral defect model according to further another embodiment of the present disclosure. The system 200 of repairing an oral defect model includes a scanner 210, a processor 220, a displayer 230 and a database 240.

The scanner 210 is configured to scan one of an oral cavity and an oral cavity model to obtain a three-dimensional oral defect model message. The processor 220 is signally connected to the scanner 210. The processor 220 receives the three-dimensional oral defect model message and includes a defect cutting line detecting module 222, a defect point selecting module 224 and a smoothing module 226. The defect cutting line detecting module 222 can perform the defect cutting line detecting steps S14, S23. Moreover, the defect point selecting module 224 is signally connected to the defect cutting line detecting module 222, and the defect point selecting module 224 can perform the defect point selecting steps S16, S24. Furthermore, the smoothing module 226 is signally connected to the defect point selecting module 224, and the smoothing module 226 performs a smoothing process at the at least one defect feature point, and converts the three-dimensional oral defect model message into a three-dimensional oral repaired model message to smooth the defect cutting line 160. The smoothing module 226 can perform the smoothing steps S18, S25. The displayer 230 is signally connected to the processor 220. The displayer 230 display the three-dimensional oral defect model message, the defect cutting line 160 and the three-dimensional oral repaired model message. Thus, the system 200 of repairing the oral defect model utilizes the smoothing process to repair the defect cutting line 160 of the defective region into a smooth edge line so as to manufacture tight artificial teeth and increase the medical quality.

According to the aforementioned embodiments and examples, the advantages of the present disclosure are described as follows.

1. The method of repairing the oral defect model of the present disclosure utilizes the smoothing process to repair the defect cutting line of the defective region into a smooth edge line, so that the uncomfortable feeling and pressure formed by a dentist obtaining an ideal model can be reduced, and deviation caused by human can also be reduced so as to manufacture tight artificial teeth and increase the medical quality.

2. The method utilizes the automation and artificial intelligence algorithm instead of conventional human experience to reduce the uncomfortable feeling and pressure formed by a dentist obtaining an ideal model, and reduces the deviation caused by human so as to manufacture tight artificial teeth and increase the medical quality.

3. The system of repairing the oral defect model utilizes the smoothing process to repair the defect cutting line of the defective region into a smooth edge line so as to manufacture tight artificial teeth and increase the medical quality.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A system of repairing an oral defect model, comprising:
a scanner configured to scan one of an oral cavity and an oral cavity model to obtain a three-dimensional oral defect model message;
a processor signally connected to the scanner, wherein the processor receives the three-dimensional oral defect model message and comprises:
   a defect cutting line detecting module, wherein the defect cutting line detecting module detects a defect cutting line of the three-dimensional oral defect model message, and the defect cutting line comprises at least one defect feature point;
   a defect point selecting module signally connected to the defect cutting line detecting module, wherein the defect point selecting module selects the at least one defect feature point of the defect cutting line; and
   a smoothing module signally connected to the defect point selecting module, wherein the smoothing module performs a smoothing process at the at least one defect feature point, and converts the three-dimensional oral defect model message into a three-dimensional oral repaired model message to smooth the defect cutting line; and
a displayer signally connected to the processor, wherein the displayer displays the three-dimensional oral defect model message, the defect cutting line and the three-dimensional oral repaired model message;
wherein the defect cutting line detecting module comprises:
   performing a sight selecting step to select an abutment region of the three-dimensional oral defect model message, and observe the abutment region from a top view of the abutment region;
   performing a projecting step to project the three-dimensional oral defect model message in the abutment region to a two-dimensional plane according to the top view of the abutment region so as to form a two-dimensional projecting point set;
   performing an interpolating step to perform an orthogonal grid interpolation method at the two-dimensional projecting point set to obtain a two-dimensional concentrated projecting point set; and
   performing a controlling point detecting step to search a feature region with an annular shape in an equal angle and a radially way out from a departure point, and then search a plurality of triangular grids of the feature region, wherein the triangular grids are viewed as a plurality of controlling points;
wherein the orthogonal grid interpolation method is an inverse distance weighted (IDW) method, and a dot density of the two-dimensional concentrated projecting point set is greater than a dot density of the two-dimensional projecting point set, and the departure point is determined as a model center of the two-dimensional concentrated projecting point set.

2. A method of repairing an oral defect model, comprising:
performing a three-dimensional oral defect model obtaining step to drive a scanner to scan an oral cavity to obtain a three-dimensional oral defect model message;
performing a defect cutting line detecting step to drive a processor to detect a defect cutting line of the three-dimensional oral defect model message, and drive a displayer to display the defect cutting line, wherein the defect cutting line comprises at least one defect feature point;
performing a defect point selecting step to select the at least one defect feature point of the defect cutting line via the displayer; and
performing a smoothing step to drive the processor to perform a smoothing process at the at least one defect feature point, and convert the three-dimensional oral defect model message into a three-dimensional oral repaired model message to smooth the defect cutting line;
wherein the defect cutting line detecting step comprises:
   performing a sight selecting step to select an abutment region of the three-dimensional oral defect model message, and observe the abutment region from a top view of the abutment region;
   performing a projecting step to project the three-dimensional oral defect model message in the abutment region to a two-dimensional plane according to the top view of the abutment region so as to form a two-dimensional projecting point set;
   performing an interpolating step to perform an orthogonal grid interpolation method at the two-dimensional projecting point set to obtain a two-dimensional concentrated projecting point set; and
   performing a controlling point detecting step to search a feature region with an annular shape in an equal angle and a radially way out from a departure point, and then search a plurality of triangular grids of the feature region, wherein the triangular grids are viewed as a plurality of controlling points;
wherein the orthogonal grid interpolation method is an inverse distance weighted (IDW) method, and a dot density of the two-dimensional concentrated projecting point set is greater than a dot density of the two-dimensional projecting point set, and the departure point is determined as a model center of the two-dimensional concentrated projecting point set.

3. The method of repairing the oral defect model of claim 2, further comprising:
performing a three-dimensional oral standard model obtaining step to obtain a three-dimensional oral standard model message from a database, wherein the three-dimensional oral standard model message is corresponding to the oral cavity;
wherein a defect difference exists between the three-dimensional oral defect model message and the three-dimensional oral standard model message, a smoothing difference exists between the three-dimensional oral repaired model message and the three-dimensional oral standard model message, and the defect difference is greater than the smoothing difference.

4. The method of repairing the oral defect model of claim 3, further comprising:
performing a deep learning step to drive the processor to perform a deep learning algorithm at the three-dimensional oral repaired model message and the three-dimensional oral standard model message so as to train the smoothing process to reduce the smoothing difference.

5. The method of repairing the oral defect model of claim 2, wherein the defect cutting line detecting step further comprises:
performing a line smoothing step to perform a weighted moving average method at the controlling points to smooth the feature region.

6. The method of repairing the oral defect model of claim 5, wherein the defect cutting line detecting step further comprises:
performing a feature cutting line generating step to generate a feature cutting line from the controlling points smoothed by the line smoothing step; and
performing a surface smoothing step to perform the weighted moving average method at the feature cutting line to generate the defect cutting line, wherein the defect cutting line is in a closed loop shape.

7. A method of repairing an oral defect model, comprising:
performing a three-dimensional oral defect model obtaining step to drive a scanner to scan an oral cavity model to obtain a three-dimensional oral defect model message;
performing a defect cutting line detecting step to drive a processor to detect a defect cutting line of the three-dimensional oral defect model message, and drive a displayer to display the defect cutting line, wherein the defect cutting line comprises at least one defect feature point;
performing a defect point selecting step to select the at least one defect feature point of the defect cutting line via the displayer; and
performing a smoothing step to drive the processor to perform a smoothing process at the at least one defect feature point, and convert the three-dimensional oral defect model message into a three-dimensional oral repaired model message to smooth the defect cutting line;
wherein the defect cutting line detecting step comprises:
performing a sight selecting step to select an abutment region of the three-dimensional oral defect model message, and observe the abutment region from a top view of the abutment region;
performing a projecting step to project the three-dimensional oral defect model message in the abutment region to a two-dimensional plane according to the top view of the abutment region so as to form a two-dimensional projecting point set;
performing an interpolating step to perform an orthogonal grid interpolation method at the two-dimensional projecting point set to obtain a two-dimensional concentrated projecting point set; and
performing a controlling point detecting step to search a feature region with an annular shape in an equal angle and a radially way out from a departure point, and then search a plurality of triangular grids of the feature region, wherein the triangular grids are viewed as a plurality of controlling points;
wherein the orthogonal grid interpolation method is an inverse distance weighted (IDW) method, and a dot density of the two-dimensional concentrated projecting point set is greater than a dot density of the two-dimensional projecting point set, and the departure point is determined as a model center of the two-dimensional concentrated projecting point set.

8. The method of repairing the oral defect model of claim 7, further comprising:
performing a three-dimensional oral standard model obtaining step to obtain a three-dimensional oral standard model message from a database, wherein the three-dimensional oral standard model message is corresponding to the oral cavity model, a defect difference exists between the three-dimensional oral defect model message and the three-dimensional oral standard model message, a smoothing difference exists between the three-dimensional oral repaired model message and the three-dimensional oral standard model message, and the defect difference is greater than the smoothing difference; and
performing a deep learning step to drive the processor to perform a deep learning algorithm at the three-dimensional oral repaired model message and the three-dimensional oral standard model message to train the smoothing process and reduce the smoothing difference.

* * * * *